United States Patent
Laugharn, Jr.

(10) Patent No.: US 10,280,395 B2
(45) Date of Patent: May 7, 2019

(54) ACOUSTIC ENERGY TREATMENT USING PHASE CHANGE COUPLANT

(71) Applicant: Covaris, Inc., Woburn, MA (US)

(72) Inventor: James A. Laugharn, Jr., Winchester, MA (US)

(73) Assignee: Covaris, Inc., Woburn, MA (US)

( * ) Notice: Subject to any disclaimer, the term of this patent is extended or adjusted under 35 U.S.C. 154(b) by 513 days.

(21) Appl. No.: 14/970,969

(22) Filed: Dec. 16, 2015

(65) Prior Publication Data

US 2016/0186126 A1    Jun. 30, 2016

Related U.S. Application Data

(60) Provisional application No. 62/096,733, filed on Dec. 24, 2014.

(51) Int. Cl.
| | |
|---|---|
| *C12N 13/00* | (2006.01) |
| *C12N 1/00* | (2006.01) |
| *C12N 1/06* | (2006.01) |
| *C12M 1/33* | (2006.01) |
| *C12M 1/00* | (2006.01) |

(52) U.S. Cl.
CPC .............. *C12N 1/066* (2013.01); *C12M 45/02* (2013.01); *C12M 47/06* (2013.01); *C12N 13/00* (2013.01)

(58) Field of Classification Search
CPC ...... C12N 11/066; C12N 1/066; C12N 13/00; C12M 45/02; C12M 47/06
USPC .................................................. 366/127, 108
See application file for complete search history.

(56) References Cited

U.S. PATENT DOCUMENTS

| | | | |
|---|---|---|---|
| 6,719,449 B1 | 4/2004 | Laugharn, Jr. et al. | |
| 6,948,843 B2 | 9/2005 | Laugharn, Jr. et al. | |
| 2008/0031094 A1* | 2/2008 | Laugharn, Jr. ...... | B01F 11/0283 367/138 |

* cited by examiner

*Primary Examiner* — Anshu Bhatia
(74) *Attorney, Agent, or Firm* — Wolf, Greenfield & Sacks, P.C.

(57) ABSTRACT

Method and apparatus for transmitting acoustic energy to a sample for treatment by employing a phase change couplant at least adjacent a sample vessel. The phase change couplant may be solid before and after treatment, but liquid during treatment to improve acoustic energy transmission charactersitics.

17 Claims, 5 Drawing Sheets

ACOUSTIC ENERGY TREATMENT USING PHASE CHANGE COUPLANT

CROSS REFERENCE TO RELATED APPLICATION

This application claims the benefit of U.S. Provisional Application No. 62/096,733, filed Dec. 24, 2014, which is hereby incorporated by reference in its entirety.

BACKGROUND

1. Field of the Invention

Systems and methods for processing of samples with acoustic energy are generally disclosed.

2. Related Art

Acoustic energy-based sample processing devices, such as Adaptive Focused Acoustic apparatuses made by Covaris of Woburn, Mass., are effective for homogenization and disruption of biological tissues, cells and other sample material. With such devices, a controlled acoustic field enables repeatable processes to be developed which often result in higher recovery of target molecules. Such target molecules may be, for example, DNA, RNA, proteins, and the like. Target molecules or other materials may be contained as samples within a vessel.

SUMMARY OF INVENTION

Aspects of the invention provide an acoustic treatment system that includes a phase change couplant that changes from solid to liquid during acoustic treatment, e.g., to enhance acoustic coupling efficiency. In an illustrative embodiment, the phase change couplant may be a solid at room temperature (i.e., 15-20 degrees C.) but change to a liquid when exposed to the acoustic energy emitted by the acoustic energy source and used to treat a sample in a vessel. The phase change couplant may be positioned adjacent the vessel, e.g., at an area where the acoustic energy passes through the vessel wall, so that the couplant may conform to the vessel wall upon phase change to liquid. That is, the inventor has found that the presence of a liquid coupling material at the vessel wall significantly enhances efficiency of transmission of at least acoustic energy, and possibly other energy, such as thermal energy. By employing a phase changing couplant that is solid before and after acoustic treatment, but liquid during treatment, the acoustic treatment system can realize the benefits of a solid coupling medium (such as ease in handling, transport and/or storage of the coupling medium) while also achieving the benefits of a liquid coupling medium during treatment (such as conformal contact between the coupling medium and a vessel).

In one aspect of the invention, an acoustic treatment device includes a vessel arranged to hold a sample to be treated with acoustic energy, and an acoustic energy source for providing acoustic energy to the sample while the sample is in the vessel. An acoustic coupling medium may be located between the acoustic energy source and the vessel to transmit the acoustic energy to the vessel. At least in part, the acoustic coupling medium may include a phase changing couplant located adjacent the vessel that is solid at room temperature, but changes to a liquid at least in a region in contact with the vessel in response to exposure to acoustic energy used the treat the sample in the vessel. After exposure of the phase changing couplant to acoustic energy is stopped, the couplant may return to a solid state. In some embodiments, the acoustic energy source may be arranged to create a focal zone of acoustic energy at the vessel, and in other embodiments the coupling medium may create the focal zone. Of course, the acoustic source and coupling medium could cooperate to create the focal zone as well.

In one embodiment, the acoustic coupling medium includes a solid and/or a liquid coupling material which may be arranged to focus acoustic energy received from the acoustic energy source. For example, the acoustic energy source may include an acoustic transducer that is flat and generates a planar wave of acoustic energy received by the coupling material, and the coupling material may focus the planar wave to form a focal zone. In some cases, a matching layer may be positioned between the acoustic transducer and the solid coupling material. Where the coupling medium includes a liquid material, a liquid impermeable membrane may be provided between the liquid coupling material and the phase changing couplant, e.g., to contain the liquid material.

Acoustic energy may be used to treat a sample for a variety of purposes and in a variety of ways. For example, the acoustic energy directed to the sample may be sufficient to cause at least one of cell lysing, compound extraction, permeabilizing, stirring, catalyzing, degrading, fluidization, heating, particle breakdown, DNA shearing, and/or disruption of molecular bonds in the sample. The volume of sample treated may vary widely as well, e.g., from 10 microliters to 150 milliliters. The acoustic energy source may be spaced from and exterior to the vessel, and the acoustic energy may have a frequency of between about 100 kilohertz and about 100 megahertz and a focal zone having a width of less than about 2 centimeters.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Figure 1:
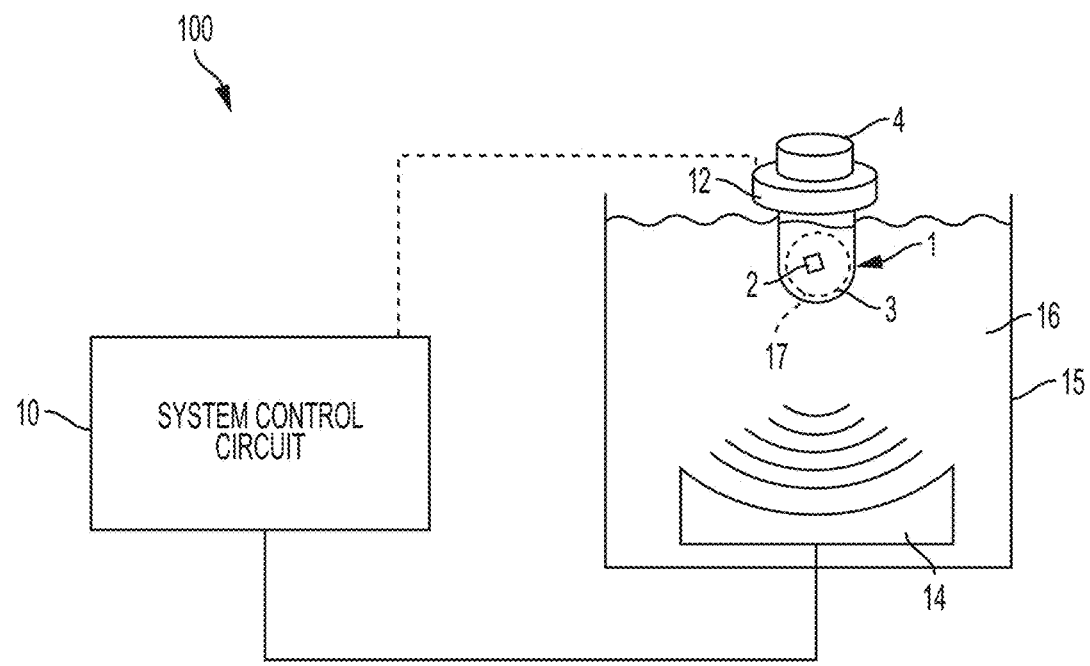
FIG. 1 shows a schematic block diagram of an acoustic treatment system that incorporates one or more aspects of the invention.

Aspects of the invention are not limited in application to the details of construction and the arrangement of components set forth in the following description or illustrated in the drawings. Other embodiments may be employed and aspects of the inventions may be practiced or be carried out in various ways. Also, the phraseology and terminology used herein is for the purpose of description and should not be regarded as limiting. Acoustic treatment systems can be useful for the homogenization and disruption of biological tissues, cells and other sample material, with the end goal of recovering target molecules from the sample material, such as DNA, RNA, proteins, and the like. In addition, such systems may be used along with aspects of the invention for DNA and/or other genomic fragment shearing, e.g., to reduce the base pair length of DNA fragments from 1,000s or 10,000s of base pairs to lengths of 200-1000 base pairs.

FIG. 1 shows a schematic block diagram of an acoustic treatment system 100 that incorporates one or more aspects of the invention and/or can be employed with one or more aspects of the invention. It should be understood that although embodiments described herein may include most or all aspects of the invention, aspects of the invention may be used alone or in any suitable combination with other aspects of the invention. In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other affects in a sample 1 contained in a vessel 4. The sample 1 may include solid particles or other material 2 and/or liquid 3. Under the control of a control circuit 10 (described in more detail below), the acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control.

The vessel 4 may have any suitable size or other arrangement, e.g., may be a glass or metal tube, a plastic container, a well in a microtiter plate, a vial, or other, and may be supported at a location by a vessel holder 12. Although a vessel holder 12 is not necessarily required, the vessel holder 12 may interface with the control circuit 10 so that the vessel 4 and the sample in the vessel is positioned in a known location relative to an acoustic field, for example, at least partially within a focal zone of acoustic energy. In this embodiment, the vessel 4 is a 130 microliter borosilicate glass tube, but it should be understood that the vessel 4 may have other suitable shapes, sizes, materials, or other feature, as discussed more below. For example, the vessel 4 may be a cylindrical tube with a flat bottom and a threaded top end to receive a cap, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes. In accordance with an aspect of the invention, the acoustic treatment system 100 may include a coupling medium that includes a phase change couplant. In an illustrative embodiment, the phase change couplant may be a solid at room temperature (i.e., 15-20 degrees C.) but change to a liquid when exposed to the acoustic energy emitted by the acoustic energy source and used to treat the sample 1 in the vessel 4. The phase change couplant may be positioned adjacent the vessel 1, e.g., at an area where the acoustic energy passes through the vessel 1 wall, so as to enhance acoustic coupling to the vessel 1. That is, the inventor has found that the presence of a liquid coupling material at the vessel where acoustic energy is transmitted to the sample significantly enhances efficiency of the transmission. For example, in some cases 25% or more acoustic energy is effectively transmitted into a vessel with a liquid coupling medium interface at the vessel wall as compared to a solid interface. By employing a phase changing couplant that is solid before and after acoustic treatment, but liquid during treatment, the acoustic treatment system can realize the benefits of a solid coupling medium (such as ease of transport, eliminated risk of spilling or evaporation of the coupling medium, avoidance of wetting a vessel with liquid coupling medium, etc.), while also achieving the benefits of a liquid coupling medium during treatment (such as improved acoustic energy transmission to the sample).

In the illustrative embodiment of FIG. 1, the coupling medium 16 includes a phase change couplant positioned between, and in contact with, the acoustic transducer 14 and the vessel 4. Materials that may be used as a phase change couplant include agarose gel, polyacrylamide gel, paraffin, low melting point metals or alloys such as gallium, indium, woods metal or others. In some cases, phase change of the couplant is caused by heating of the couplant by the acoustic energy. In other circumstances, the acoustic energy itself may cause the phase change without significant change in temperature. In the embodiment of FIG. 1, the coupling medium 16 includes a phase change couplant, such as polyacrylamide gel, contained in a container 15. At room temperature, the phase change couplant is solid, and the vessel 1 may be positioned in the couplant, e.g., into a depression formed in the phase change couplant. The transducer 14 may then be caused to generate acoustic energy, which forms a focal zone 17 at or near the sample 1, the vessel 4 and/or a portion of the couplant adjacent the vessel 1. The acoustic energy causes the portion of the phase change couplant adjacent the vessel 4 to change to a liquid, thereby enhancing transmission of acoustic energy from the couplant to the vessel 4. Although a portion of the couplant near the vessel 4 may turn to a liquid, other portions of the couplant further from the vessel 4 may remain solid. Once acoustic treatment is stopped, the vessel 4 may be removed from the coupling medium 16 and the phase change couplant may return to a solid. Conversion of the couplant to a solid may help avoid the presence of a liquid on the exterior of the vessel 4, thus helping to avoid dripping of coupling liquid in unwanted locations.

Figure 2:
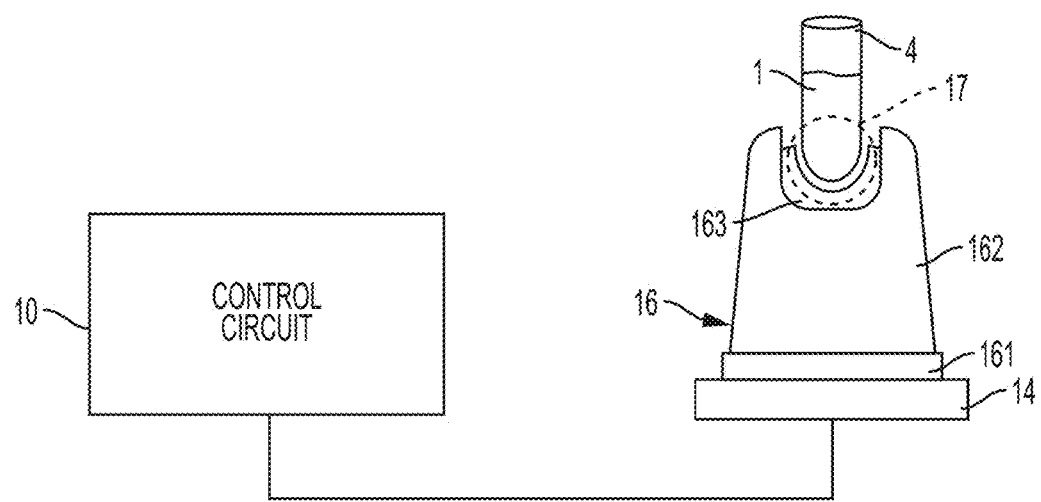
FIG. 2 shows a schematic block diagram of another acoustic treatment system that incorporates a solid waveguide.

FIG. 2 shows another illustrative embodiment that incorporates one or more aspects of the invention. In this embodiment, the transducer 14 includes a flat element that creates a planar wave of acoustic energy. For example, the transducer 14 may include one or more piezoelectric elements that have a flat or planar face from which acoustic energy is emitted. To create a focal zone 17, a waveguide 162 is arranged to receive the acoustic energy from the transducer 14 and suitably focus the energy to create the focal zone 17. In this embodiment, the waveguide 162 is formed of a graphite material, although other arrangements are possible in which one or more materials are used to form the waveguide 162. This embodiment also includes a matching layer 161 between the transducer 14 and the waveguide 162 so that acoustic energy is better transmitted to the waveguide 162. That is, in this embodiment, an impedance difference between the transducer 14 and the waveguide 162 may cause scattering or other attenuation of acoustic energy, and the matching layer 161 helps to bridge the transition in a way to reduce attenuation. In this embodiment, the matching layer 161 may include a glass ceramic, such as Macor (a trademark of Corning Inc.), or other suitable material. Of course, the matching layer 161 is not required, and in some embodiments two or more matching layers may be used. The matching layer 161 may be adhered (e.g., by epoxy) or otherwise attached to both the transducer 14 and the waveguide 162, although other arrangements are possible, such as clamping the waveguide 162 and transducer 14 together using an external fixture.

A phase change couplant 163 may be located between the waveguide 162 and the vessel 4 to provide a desired acoustic coupling between the waveguide 162 and the vessel 4. In this embodiment, the waveguide 162 is arranged to include a depression or pocket into which the vessel 4 may be positioned, and the phase change couplant 163 is arranged to effectively line the inner wall of the depression. Of course, other arrangements are possible. For example, the depression is not required, and instead the waveguide 162 may include a flat surface on which the vessel 4 is positioned. The phase change couplant 163 may be positioned between the vessel 4 and the waveguide 162, e.g., as a flat layer or otherwise configured. Although a gap is shown in FIG. 2 between the vessel 4 and the phase change couplant 163, such a gap need not be provided, and instead the vessel 4 may fit relatively tightly into the space defined by the couplant 163. As will be understood, however, upon beginning of acoustic treatment, at least a portion of the phase change couplant 163 will convert to a liquid and fill gaps between the vessel 4 and the couplant 163, at least near a bottom of the vessel 4. As shown in FIG. 2, the focal zone 17 may overlap a portion of the phase change couplant 163 to help aid in the transition between solid and liquid. In one embodiment, the waveguide 162 terminates approximately 1-3 mm proximal of the focal zone 17 (i.e., on a side closer to the transducer 14) with the transducer 14 operating to generate acoustic energy at a frequency of about 500 kHz.

Figure 3:
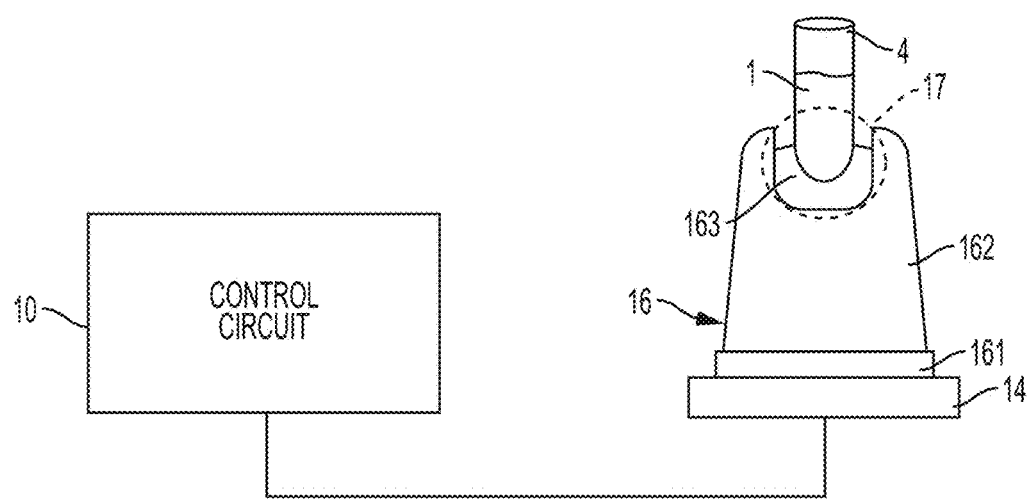
FIG. 3 shows a schematic block diagram of another acoustic treatment system that incorporates a waveguide including a liquid medium.

FIG. 3 shows an embodiment similar to that in FIG. 2, except that instead of having a waveguide 162 that includes a solid material (e.g., graphite), the waveguide 162 has a liquid material, such as water. For example, the waveguide 162 may be formed to include a solid shell or skin, e.g., made of a silicone rubber or polymethylpentene material, that contains a volume of water. This assembly may function to focus acoustic energy from the transducer 14 to form a desired focal zone 17. As in the FIG. 2 embodiment, the phase change couplant 163 may be arranged at a location on the waveguide 162 where acoustic energy exits the waveguide 162 for transmission to the vessel 4. This arrangement may be advantageous in relatively high power treatment applications, e.g., because the liquid waveguide material may more rapidly absorb heat from the vessel 4 and/or phase change couplant 163 than a solid material. In some cases, the liquid waveguide coupling material may be exchanged, e.g., relatively warm liquid may be removed from the waveguide 162 and replaced with cooler liquid. The waveguide liquid may be cooled by a heat exchanger or other chiller arrangement.

Figure 4:
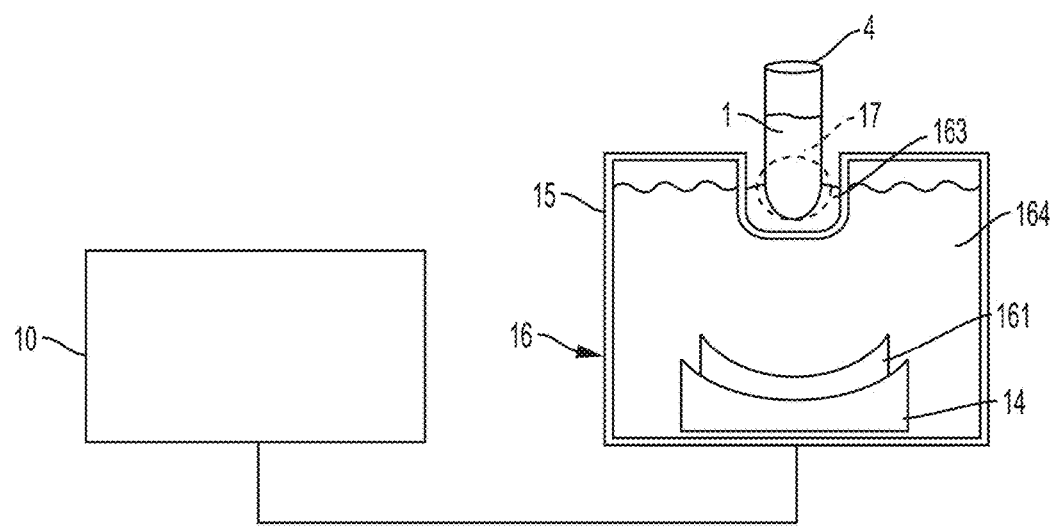
FIG. 4 shows a schematic block diagram of another acoustic treatment system that incorporates a coupling medium container including a liquid medium.

FIG. 4 shows another embodiment of an acoustic treatment system 100 that incorporates one or more aspects of the invention. In this embodiment, the transducer 14 is arranged to itself create the focal zone 17, i.e., the transducer 14 creates an acoustic wavefront that forms the desired focal zone 17 as in the FIG. 1 embodiment. However, in this embodiment, the coupling medium 16 includes a liquid medium 164, such as water, that transmits acoustic energy from the transducer 14 and an optional matching layer 161. A container 15 holds the liquid medium 164 and includes a wall (in this case at the top of the container 15) at which the phase change couplant 163 is located. In this embodiment, the container 15 includes a depression or pocket in which the phase change couplant 163 is located and the vessel 4 is received. However, this arrangement is not required, e.g., the phase change couplant 163 may be arranged on a flat or protruding portion of the container 15 wall, and the vessel 4 may be positioned adjacent the phase change couplant 163. The portion of the container 15 where acoustic energy exits the coupling medium 16 for transmission to the phase change couplant 163 and the vessel may be arranged as an acoustic window, e.g., may be relatively transparent to acoustic energy. Thus, other portions of the container 15 may be relatively opaque or translucent to acoustic energy.

Figure 5:
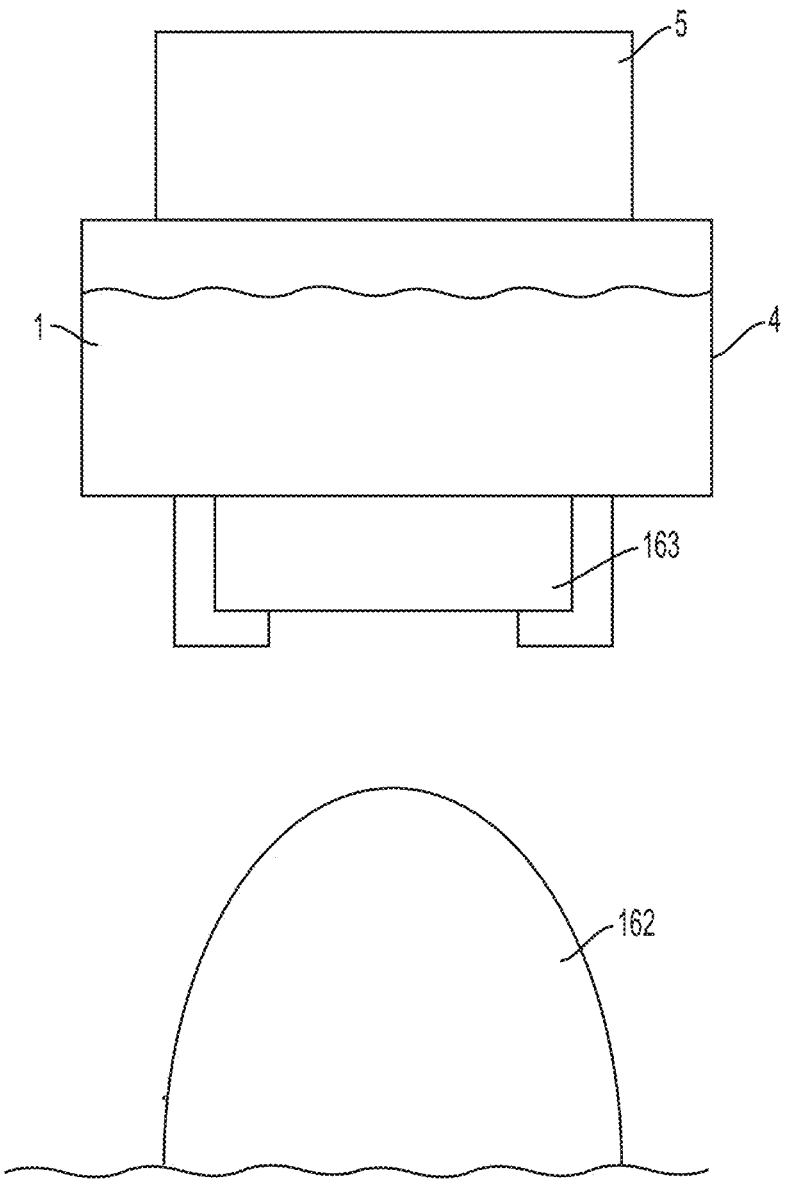
FIG. 5 shows an embodiment of a vessel having an attached phase change couplant.

While the embodiments above illustrate arrangements in which the phase change couplant is attached to a waveguide 162 or other portions of the coupling medium, such an arrangement is not required. For example, FIG. 5 shows an illustrative embodiment in which a phase change couplant 163 is attached to a vessel 4. While in this embodiment, the phase change couplant 163 is shown attached to a bottom of a rectangularly shaped vessel 4 by a wall that depends from the bottom of the vessel 4, other arrangements are possible. For example, the couplant 163 may be arranged as a film adhered to the vessel 4, e.g., a piece of Parafilm M or similar material may be adhered to a portion of the vessel 4. Also, the couplant 163 may be shaped in any suitable way, e.g., may be arranged to cover the hemispherically shaped bottom of a sample tube. In this arrangement, the vessel 4 may be positioned so that the couplant 163 contacts another portion of the coupling medium 16, such as a portion of a waveguide 162 as shown. Alternately, the couplant 163 may be positioned adjacent to an acoustic window of the coupling medium 16 or other component that transmits acoustic energy from a transducer 14, such as a matching layer. An optional cooling device 5, such as thermoelectric device, heat exchanger, etc., may be arranged to remove heat from the vessel 4 during treatment. With exposure to acoustic energy during treatment, a portion of the couplant 163 may convert to liquid, but some portions of the couplant 163, such as those radially outward from the main path of acoustic energy, may remain solid. Thus, the couplant 163 may be retained in contact with the vessel 4 by solid portions being held in place, surface tension or cohesion, and/or other mechanisms. Once treatment is complete, the liquid portions of the couplant 163 may revert to a solid.

In some cases, the phase change couplant may be more efficient at higher frequencies since attenuation of acoustic energy by the couplant increases as frequency increases. Also, at higher frequencies the diameter of the focal zone can be smaller and have a higher acoustic energy density. For example, at 1.1 MHz the maximum diameter of a focal zone 17 may be 3 mm. With a phase change couplant 163 in the FIG. 5 embodiment being arranged as a disc with a 15 mm diameter, a center of the couplant disc may be liquefied during acoustic treatment, but areas of the couplant around the center may be solid since the temperature of the couplant in these areas is below the melting point.

To control an acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. An acoustic treatment device, comprising:
a vessel arranged to hold a sample to be treated with acoustic energy;
an acoustic energy source for providing acoustic energy to the sample while the sample is in the vessel and separated from the acoustic energy source, the acoustic energy having a focal zone located at the vessel; and
an acoustic coupling medium between the acoustic energy source and the vessel, the acoustic coupling medium including a phase changing couplant located adjacent an exterior of the vessel and being solid at room temperature, the phase changing couplant changing to a liquid at least in a region in contact with the vessel in response to exposure to acoustic energy used the treat the sample in the vessel and returning to a solid state after exposure of the phase changing couplant to acoustic energy is stopped.

2. The device of claim 1, wherein the acoustic coupling medium includes a solid coupling material between the acoustic energy source and the phase changing couplant.

3. The device of claim 2, wherein the solid coupling material is arranged to focus acoustic energy received from the acoustic energy source.

4. The device of claim 3, wherein the acoustic energy source includes an acoustic transducer that is flat and generates a planar wave of acoustic energy received by the solid coupling material.

5. The device of claim 4, further comprising a matching layer between the acoustic transducer and the solid coupling material.

6. The device of claim 1, wherein the acoustic coupling medium includes a liquid coupling material between the acoustic energy source and the phase changing couplant.

7. The device of claim 6, wherein the liquid coupling material is water.

8. The device of claim 7, wherein the liquid coupling material is arranged to focus acoustic energy received from the acoustic energy source.

9. The device of claim 8, wherein the acoustic energy source includes an acoustic transducer that is flat and generates a planar wave of acoustic energy received by the liquid coupling material.

10. The device of claim 9, further comprising a matching layer between the acoustic transducer and the liquid coupling material.

11. The device of claim 6, comprising a liquid impermeable membrane between the liquid coupling material and the phase changing couplant.

12. The device of claim 11, wherein the impermeable membrane includes a silicone rubber or polymethylpentene (TPX) material.

13. The device of claim 1, wherein the acoustic coupling medium defines a vessel holder arranged to support the vessel at a location at least partially in the focal zone of the acoustic energy.

14. The device of claim 1, wherein the acoustic energy directed to the sample is sufficient to cause at least one of lysing, extraction, permeabilizing, stirring, catalyzing, degrading, fluidization, heating, particle breakdown, DNA shearing, or disruption of molecular bonds in the sample.

15. The device of claim 1, wherein the acoustic energy source is spaced from and exterior to the vessel, and the acoustic energy comprises a frequency of between about 100 kilohertz and about 100 megahertz and a focal zone having a width of less than about 2 centimeters, and wherein at least a portion of the acoustic energy is adapted to propagate exterior to the vessel.

16. The device of claim 1, wherein the acoustic energy source includes an acoustic transducer having a dome shape and arranged to generate focused acoustic energy to create the focal zone.

17. The device of claim 1, wherein the sample has a volume of 10 microliters to 150 milliliters.

* * * * *